United States Patent [19]

Tsuda et al.

[11] Patent Number: Plant 6,899

[45] Date of Patent: Jul. 4, 1989

[54] PETUNIA PLANT NAMED 'REVOLUTION BRILLIANTPINK-MINI'

[75] Inventors: Shinzo Tsuda; Hiroshi Hirabayashi, both of Yachiyo, Japan

[73] Assignees: Suntory Limited, Osaka; Keisei Rose Nurseries, Inc., Tokyo, both of Japan

[21] Appl. No.: 178,163

[22] Filed: Apr. 6, 1988

[30] Foreign Application Priority Data

Oct. 1, 1987 [JP] Japan ..... 62-2479

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Armstrong, Nikaido, Marmelstein, Kubovcik & Murray

[57] ABSTRACT

Disclosed herein is a decumbent type petunia plant having long stems. The plant has abundant branching and a great profusion of blooms, and the whole bush remains in bloom for a considerable period of time. The flowers are single and relatively small and the petals have a metallic luster and a strong reddish purple color with dark reddish purple lines radiating from a moderate purple center portion. The plant is highly resistant to rain, heat, and drought.

4 Drawing Sheets

BACKGROUND OF THE VARIETY

The present invention relates to a new and distinct variety of petunia plant obtained from crossing 'Recoverer Blue (♀)' and a wild type of petunia plant (♂) native to Brazil.

Petunia is a very popular plant and is used for flower bedding and potting in the summer season. There only a few varieties of the petunia plant which do not have an upright growth habit and which have a high resistance to rain, heat, and drought. Accordingly, this invention was aimed at obtaining a new variety of decumbent type petunia plant having long stems, the bush remaining in bloom for a considerable period of time, and a high resistance to rain, heat and drought.

The new variety of petunia plant according to this invention originated from a crossing of 'Recoverer Blue' as the female parent and a wild type of petunia plant native to Brazil as the pollen parent, in June, 1985 at the Yachiyo Farm of Keisei Rose Nurseries, Inc., residing at 755 Ōwadasinden, Yachiyo-shi, Chiba-Ken, Japan. From this crossing, 250 seedlings were obtained in 1986, from which 3 seedlings were selected, propagated by cutting, and then grown as a trial by flower bedding. Only one of the 3 resulting plants was selected. The botanical characteristics of the finally-selected plant were then examined, using a similar variety, female parent 'Recoverer Blue', for comparison, from the spring of 1987. As a result, it was concluded that this petunia plant is distinguishable from any other variety, whose existence is known to us, and this new variety of petunia plant was named 'Revolution Brilliantpink-Mini'.

In the following description, the color-coding is in accordance with the Horticultural Colour Chart of The Royal Horticultural Society, London, England (R.H.S. Colour Chart), and the Inter-Society Color Council-Nation Bureau of Standards Color Name (ISCC-NBS Color Name). A color chart based on The Japan Color Standard for Horticultural Plant (JHS Color Chart) is also added for reference.

'Recoverer Blue', used as the female parent in the breedng of this new variety 'Revolution Brilliantpink-Mini', is one of the Recoverer Series bred by the Sakata Seed Corp., Japan. The Recoverer Series includes 'Recoverer Scarletred', 'Recoverer White', and 'Recoverer Pink', and these plants are commonly characterized by a high resistance to rain. The main botanical characteristics of 'Recoverer Blue' are as follows.

Plant:

*Growth habit.*—Upright.

*Plant height.*—30–40 cm.

*Spreading area of plant.*—25–35 cm in diameter.

*Blooming period.*—April to September in the southern Kantō area, Japan.

Stem:

*Thickness.*—Main stem 4.0–6.0 mm; lateral stem 2.0–3.0 mm.

*Color.*—Brilliant yellow green (RHS 145B, JHS 3504-3503).

*Branching.*—Abundant.

*Pubescence.*—Normal.

*Length of internode.*—2.0–3.0 cm before blooming; 2.0–4.0 cm during blooming.

Leaf:

*Phyllotaxis.*—Verticillate before blooming; opposite during blooming.

*Shape.*—Oval.

*Size (average).*—4.5–5.0 cm×2.0–3.0 cm.

*Thickness.*—0.3–0.5 mm.

*Color.*—Moderate olive green to moderate yellow green (RHS 146A–137C, JHS 3508–3712).

*Pubescence.*—Normal.

Flower: Opening obliquely upward.

*Type.*—Single.

*Shape.*—Funnel-shape, with five-fissured limb.

*Diameter.*—8.0–8.5 cm.

*Color.*—In the unopened stage (bud), dark reddish purple to black (RHS 79A–202A, JHS 8618--05); both when open and at full bloom, deep purple (RHS 83A, JHS 8606–8609).

*Reproductive organs.*—1 normal pistil having a strong yellow green (RHS 143A, JHS 3711) stigma, and 5 normal stamens each having a medium gray (RHS 202B–202C, JHS-03--02) anther and a light purple (RHS 87B–87C, JHS 8304) filament.

*Peduncle.*—1.5–2.5 mm in thickness, and 2.5–3.0 cm in length.

Physiological and ecological characteristics: High resistance to rain, heat, and disease, and moderate resistance to pest.

The male parent used in the breeding of 'Revolution Brilliantpink-Mini' is a wild type of petunia native to Brazil, the seeds of which were gathered at Gramado, Rio Grande Do Sul, Brazil and introduced to Japan in October, 1983. This wild type of plant is presently maintained at the aforementioned Yachiyo Farm of the Keisei Rose Nurseries, Inc. The main botanical characteristics of this male parent are as follows.

Plant:

*Growth habit.*—Decumbent.

*Plant height.*—20 cm.

*Spreading area of plant.*—100–150 cm in diameter.

*Blooming period.*—May to August in the southern Kanto area, Japan.

Stem:

*Length from base.*—50–80 cm.

*Thickness.*—Main stem 2.0–3.0 mm; lateral stem 1.5–2.5 mm.

*Color.*—Strong yellow green (RHS 144B–144C, JHS 3512–3513).

*Branching.*—Over-abundant.

*Pubescence.*—Many.

*Length of internode.*—1.0–2.0 cm before blooming; 1.5–3.0 cm during blooming.

Leaf:

*Phyllotaxis.*—Opposite both before and during blooming.

*Shape.*—Oval.

*Size (average).*—4.5–5.5 cm×2.5–3.5 cm.

*Thickness.*—0.4–0.5 mm.

*Color.* Grayish olive green (RHS 137A–137B, JHS 3716–3717).

*Pubescence.*—Few.

Flower: Opening obliquely upward.

*Type.*—Single.

*Shape.*—Funnel-shape, with five-fissured limb.

*Diameter.*—4.0–5.0 cm.

*Color.*—In the unopened stage (bud), dark reddish purple (RHS 79B, JHS 8907–8909); when open, vivid reddish purple (RHS 74A, JHS 9207); at full bloom, vivid reddish purple (RHS 80A, JHS 8906).

*Reproductive organs.*—1 pistil and 5 stames, both normal.

*Peduncle.*—0.9–1.2 mm in thickness, and 2.0–2.5 cm in length.

Physiological and ecological characterstics: High resistance to cold, relatively high resistance to heat, and moderate resistance to disease and pest.

This new and distinct variety of petunia plant, 'Revolution Brilliantpink-Mini', was asexually reproduced by cutting at the aforementioned Yachiyo Farm of Keisei Rose Nurseries, Inc., and the homogeniety and stability thereof were confirmed.

SUMMARY OF THE INVENTION

The new variety of petunia plant has a decumbent habit and long stems, and thus is very different from a similar variety, 'Recoverer Blue' female parent, having an upright growth habit. The plant has abundant branching and a great profusion of blooms, and the whole bush remains in bloom for a considerable period of time, longer than the blooming period of 'Recoverer Blue'. The flowers are single and relatively small, and smaller than 'Recoverer Blue', and the petals have a metallic luster and a strong reddish purple color, which is lighter than the deep purple of 'Recoverer Blue', with dark reddish purple lines radiating from a moderate purple center portion. The plant is highly resistant to rain, heat, and drought.

DESCRIPTION OF THE VARIETY

Figure 1:
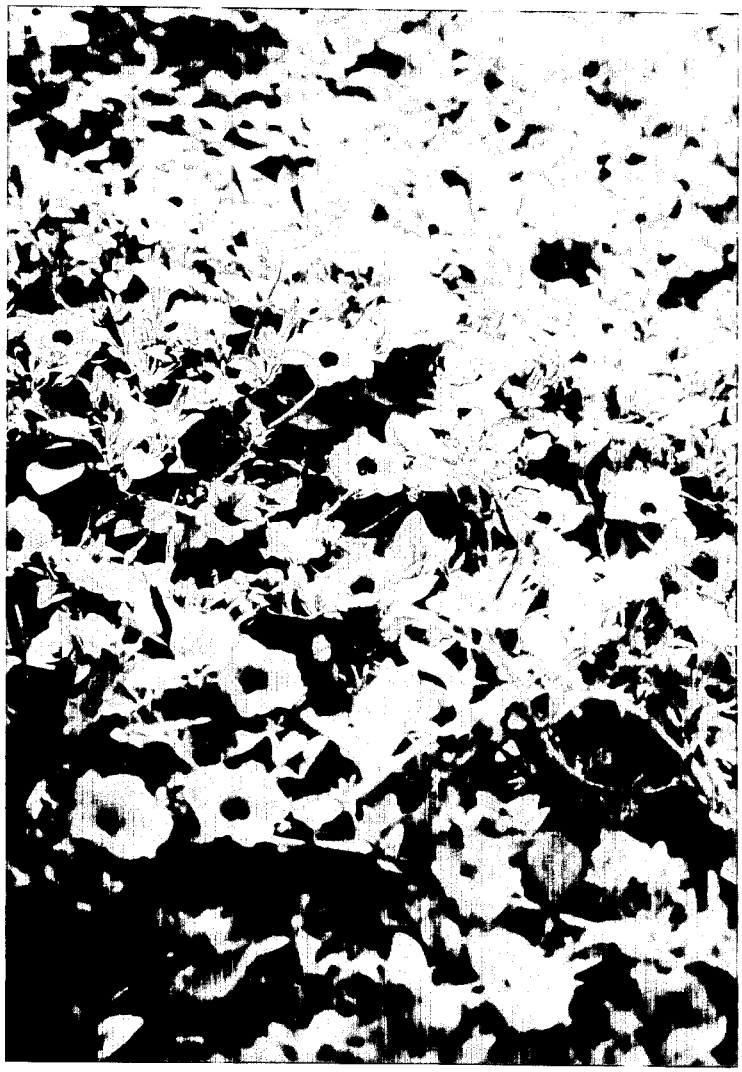
FIG. 1 is a photograph giving a partial view of the new variety of petunia plant planted in a flower bed.
Figure 2:
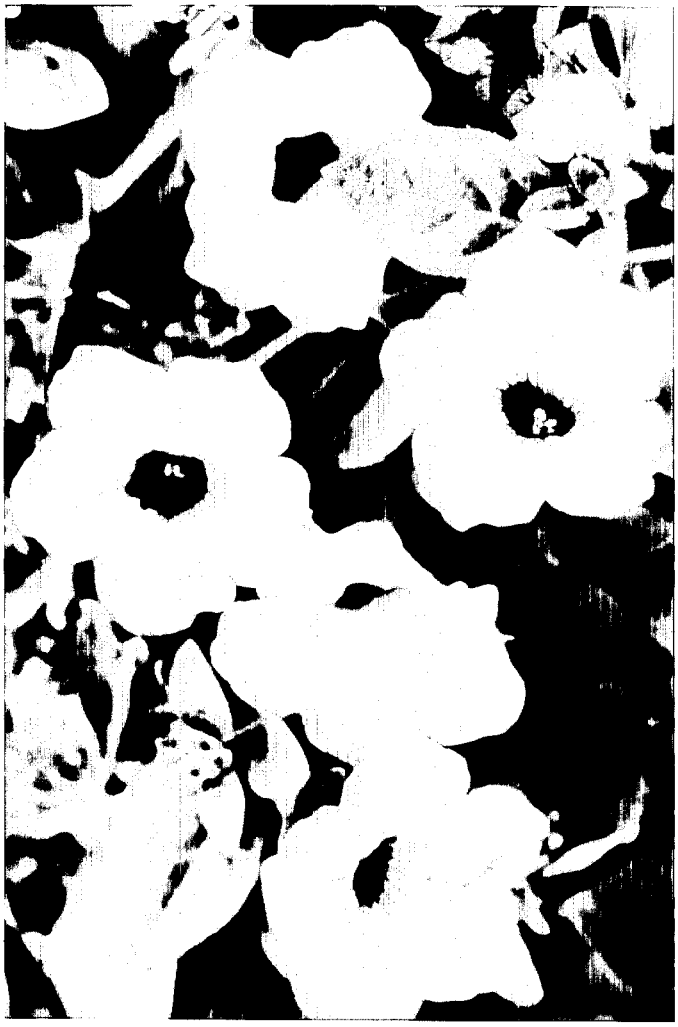
FIG. 2 is a photograph of flowers of the new variety of petunia plant.
Figure 3:
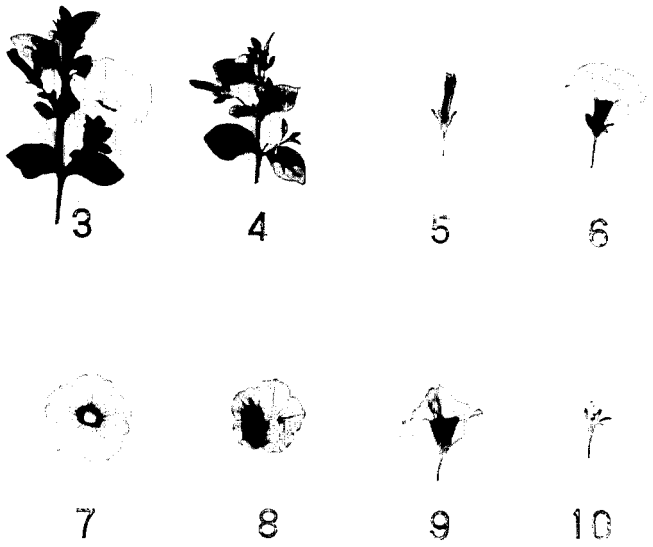
FIG. 3 is a photograph showing, in numerical order, a branch having an open flower (3), a current shoot (4), a bud (5), a side view of the flower (6), a front view of the flower (7), a rear view of the flower (8), an interior view of the flower (9), and pistil and stamens (10), of the new variety petunia plant.
Figure 4:
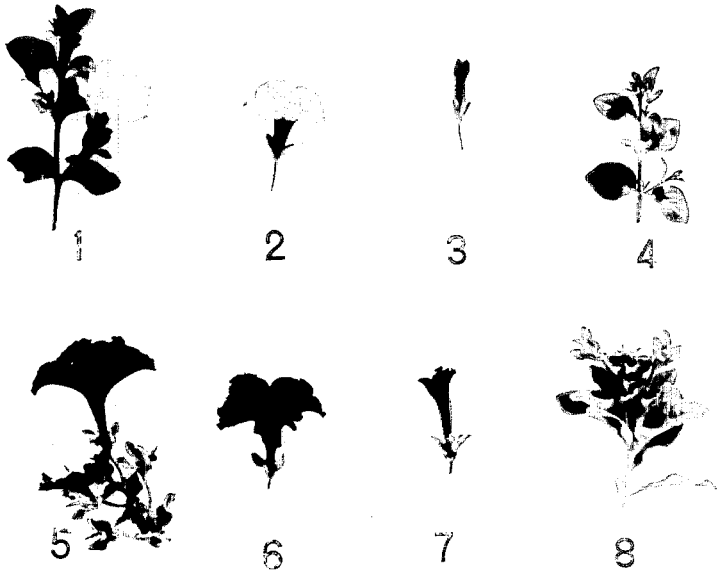
FIG. 4 is a photograph showing, in numerical order, a branch having an open flower (1), a flower (2), a bud (3) and a current shoot (4) of the new variety of petunia plant, in comparison with corresponding items (5–8) of a similar variety, 'Recoverer Blue'.

The botanical characteristics of the new and distinct variety of petunia plant 'Revolution Brilliantpink-Mini' are as follows.

Plant:

*Growth habit.*—Decumbent. The stems hang down when potted in a hanging pot.

*Plant height.*—15–20 cm.

*Spreading area of plant.*—The stem extends to a length of 50–80 cm from the base, and thus the spreading area of the plant is 100–150 cm in diameter.

*Growth.*—Very vigorous with abundant branching, a great profusion of blooms; the whole bush remaining in bloom for a considerable period of time.

*Blooming period.*—Late March to late September, in the southern Kantö area, Japan. The plant shape does not change throughout this period.

Stem:

*Thickness.*—main stem 3.0–5.0 mm; lateral stem 2.0–3.0 mm.

*Color.*—Moderate yellow green (RHS 146B–146C, JHS 3513-3312).

*Pubescence.*—Normal.

*Branching.*—Over-abundant.

*Length of internode.*—1.5–2.5 cm before blooming; 4.0–6.0 cm during blooming.

Leaf:

*Phyllotaxis.*—Verticillate before blooming; opposite during blooming.

*Shape.*—Lancet.

*Size (average).*—4.0–5.0 mm×2.5–3.0 cm.

*Thickness.*—0.4–0.5 mm.

*Color.*—Strong yellow green to moderate olive green (RHS 144A–146A, JHS 3707–3508).

*Pubescence.*—Few.

Flower: Opening obliquely upward.

Type.—Single.

Shape.—Funnel-shape, with five-fissured limb.

*Diameter.*—5.0–5.5 cm, relatively small.

*Color.*—In the unopened stage (bud), dark reddish purple (RHS 79A–79B, JHS 8909–9210); when open, strong reddish purple (RHS 72A–72B, JHS 9207–9208); at full bloom, strong reddish purple (RHS 72A–72B, JHS 9207–9208), with dark reddish purple (RHS 79A, JHS 9218) lines radiating from a moderate purple (RHS 86C–86D, JHS 8611) center portion. The reverse side of the petal is a vivid to strong reddish purple color (RHS 78A–78B, JHS 8905–8904). The petal has a metallic luster.

*Reproductive organs.*—1 normal pistil having a grayish olive green (RHS 137A–137B, JHS 3716) stigma, and 5 normal stamens each having a brilliant purple (RHS 91A–91B, JHS 8305) anther and a light purple (RHS 87D, JHS 8603) filament.

*Peduncle.* 1.0–1.5 mm in thickness, and 2.0–3.0 cm in length.

Physiological and ecological characteristics: High resistance to rain, heat, and drought. Also high resistance to disease, particularly gray mold (Botrytis). Moderate resistance to pest.

This new variety of petunia plant is most suitable for flower bedding and potting, particularly in hanging pots or planters, and further excellent for ground cover.

The plant of this new variety 'Revolution Brilliant-pink-Mini' is presently planted and maintained at the Yachiyo Farm of the Keisei Rose Nurseries, Inc., residing at 755 Öwadasinden, Yachiyo-shi, Chiba-ken, Japan.

We claim:

1. A new and distinct variety of petunia plant, substantially as herein illustrated and described, characterized particularly as to novelty by (A) being a decumbent habit plant having long stems, (B) an abundant branching and a great profusion of blooms, the whole bush remaining in bloom for a considerable period of time, (C) flowers that are single and relatively small, the petals having a metallic luster and a strong reddish purple color with dark reddish purple lines radiating from a moderate purple center portion, and (D) a high resistance to rain, heat, and drought.

* * * * *